(12) United States Patent
Douglas et al.

(10) Patent No.: US 9,181,313 B2
(45) Date of Patent: Nov. 10, 2015

(54) TREATMENT AND PREVENTION OF MALARIA

(75) Inventors: Alexander Douglas, Oxford (GB); Simon Draper, Oxford (GB); Adrian Hill, Oxford (GB); Andrew Williams, Oxford (GB); Joseph Illingworth, Matlock (GB)

(73) Assignee: ISIS INNOVATION LIMITED, Oxford (GB)

( * ) Notice: Subject to any disclaimer, the term of this patent is extended or adjusted under 35 U.S.C. 154(b) by 42 days.

(21) Appl. No.: 13/823,979

(22) PCT Filed: Feb. 24, 2012

(86) PCT No.: PCT/GB2012/050433
§ 371 (c)(1),
(2), (4) Date: Mar. 15, 2013

(87) PCT Pub. No.: WO2012/114125
PCT Pub. Date: Aug. 30, 2012

(65) Prior Publication Data
US 2013/0183332 A1 Jul. 18, 2013

(30) Foreign Application Priority Data
Feb. 25, 2011 (GB) .................................. 1103293.5

(51) Int. Cl.
| | | |
|---|---|---|
| *C07K 14/445* | (2006.01) | |
| *A61K 39/39* | (2006.01) | |
| *A61K 39/015* | (2006.01) | |
| *C07K 16/20* | (2006.01) | |
| *C12N 15/115* | (2010.01) | |
| *A61K 39/00* | (2006.01) | |

(52) U.S. Cl.
CPC ............. *C07K 14/445* (2013.01); *A61K 39/015* (2013.01); *A61K 39/39* (2013.01); *C07K 16/205* (2013.01); *C12N 15/115* (2013.01); *A61K 2039/507* (2013.01); *A61K 2039/53* (2013.01); *C07K 2317/76* (2013.01); *C12N 2310/16* (2013.01)

(58) Field of Classification Search
None
See application file for complete search history.

(56) References Cited

FOREIGN PATENT DOCUMENTS

| WO | WO 2005/018665 | * | 3/2005 |
|---|---|---|---|
| WO | 2010/022452 | | 3/2010 |
| WO | WO 2010/022452 | * | 3/2010 |
| WO | 2012/046081 | | 4/2012 |

OTHER PUBLICATIONS

Vaughn et al (Current Opinion in Immunology 2012, 24:324-331).*
Struik and Riley, Immunological Reviews 201:268-290, 2004.*
Baum et al. (2009) "Reticulocyte-Binding Protein Homologue 5—An Essential Adhesin Involved in Invasion of Human Erythrocytes by Plasmodium Falciparum;" International Journal of Parasitology; 39;371-380.
Draper et al. (2010) "Enhancing Blood-Stage Malaria Subunit Vaccine Immunogenicity in Rhesus Macaques by Combining Adenovirus, Poxvirus, and Protein-In-Adjuvant Vaccines;" Journal of Immunology; 185:7583-7595.
International Search Report for PCT/GB2012/050433, WO2012/114125; Jan. 30, 2013.
Rodriguez et al. (2008) "PFRH5: A Novel Reticulocyte-Binding Family Homolog of Plasmodium Falciparum That Binds to the Erythrocyte, and an Investigation of Its Receptor;" PLOS One; 3:E3300.
Sridhar et al. (2008) "Single-Dose Protection Against Plasmodium Berghei by a Simian Adenovirus Vector Using a Human Cytomegalovirus Promoter Containing Intron A;" 82:3822-3833
Chinese Office Action for Application No. 201280010331.2, issued Jul. 7, 2014, State Intellectual Property Office of People's Republic of China.
English language translation of Chinese Office Action for Application No. 201280010331.2, issued Jul. 7, 2014, State Intellectual Property Office of People's Republic of China (document NPL6).
Douglas et al., PfRH5 vaccine efficacy against heterologous strain bloodstage Plasmodium falciparum, The Lancet, Poster 64, p. 43 (available online Feb. 26, 2014).
Douglas et al., A PfRH5-Based Vaccine Is Efficacious against Heterologous Strain Blood-Stage Plasmodium falciparum Infection in Aotus Monkeys, Cell Host & Microbe 17:130-139 (Jan. 2015).
Singh et al., Immunity to Recombinant Plasmodium falciparum Merozoite Surface Protein 1 (MSP1): Protection in Aotus nancymai Monkeys Strongly Correlates with Anti-MSP1 Antibody Titer and In Vitro Parasite-Inhibitory Activity, Infection and Immunity, 74(8):4573-4580 (2006).
Stowers et al., Vaccination of Monkeys with Recombinant Plasmodium falciparum Apical Membrane Antigen 1 Confers Protection against Blood-Stage Malaria Infection and Immunity 70(2):6961-6967(2002).
Deans et al., Rat monoclonal antibodies which inhibit the in vitro multiplication of Plasmodium knowlesi Clin. Exp. Immunol. 49: 297-309 (1982).
Wright et al., Structure of malaria invasion protein RH5 with erythrocyte basigin and blocking antibodies Nature 515 (7527): 427-430 (2014).

* cited by examiner

*Primary Examiner* — Oluwatosin Ogunbiyi
(74) *Attorney, Agent, or Firm* — Nevrivy Patent Law Group P.L.L.C.

(57) ABSTRACT

There are provided antigens, vectors encoding the antigens, and antibodies and other binding compounds to the antigens and uses thereof in the prevention or treatment of malaria. In particular, compositions are provided comprising a Reticulocyte-binding protein Homologue 5 (PfRH5) antigen having at least 90% identity with SEQ ID NO: 1, or a fragment thereof; or which comprise a viral vector that expresses PfRH5 antigen having at least 90% identity with SEQ ID NO: 2, or a fragment thereof.

10 Claims, 9 Drawing Sheets

Figure 1:
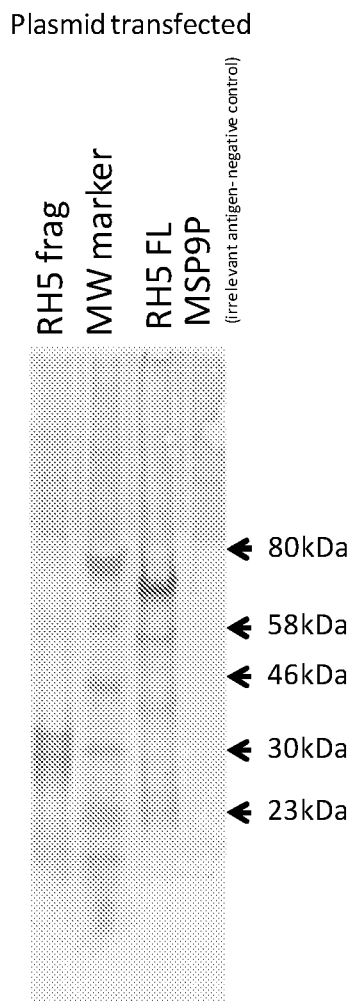

FIGURE 5A
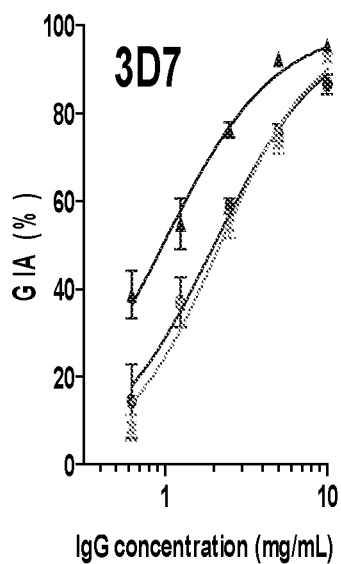
FIGURE 5B
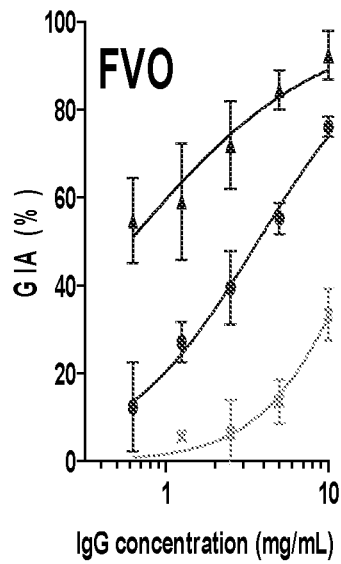
FIGURE 5C
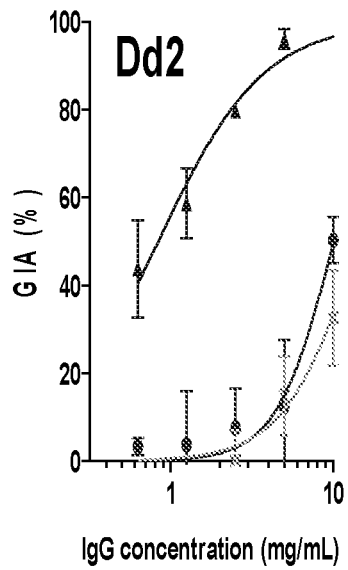
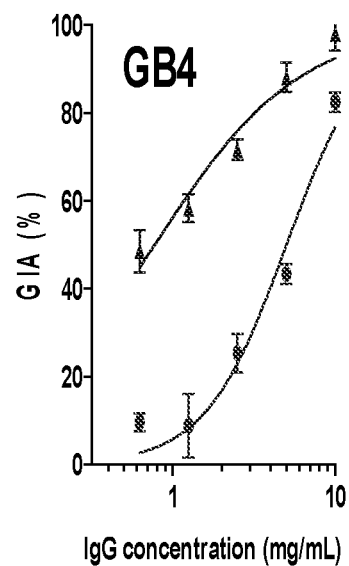
FIGURE 5D
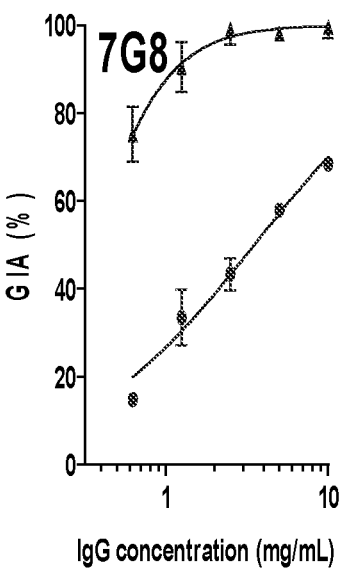
FIGURE 5E
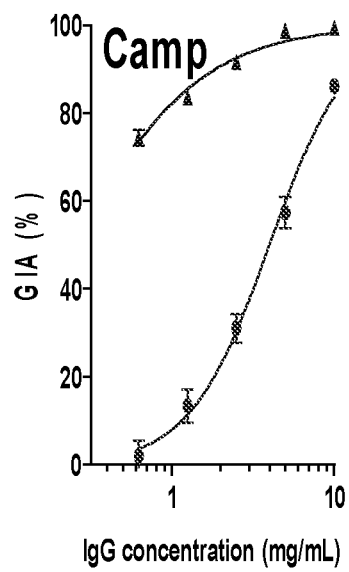
FIGURE 5F

TREATMENT AND PREVENTION OF MALARIA

REFERENCE TO A SEQUENCE LISTING SUBMITTED ELECTRONICALLY VIA EFS-WEB

The content of the sequence listing (Name: Sequence_listing.txt, Size: 9,106 bytes; and Date of Creation: Mar. 11, 2013) electronically submitted via EFS-Web is incorporated by reference in its entirety.

The present invention relates to antigens, antibodies and vaccines for treatment or prevention of malaria.

The infection of red blood cells (RBCs) by the blood-stage form of the *Plasmodium* parasite is responsible for the clinical manifestations of malaria. Examples of *Plasmodium* parasite include the species *P. falciparum, P. vivax, P. ovale* and *P. malariae*. The parasite of particular interest is *P. falciparum*, as it is this parasite which causes the most lethal infections since it can infect RBCs of all ages and is not limited to immature RBCs. *P. falciparum* alone is responsible for around a million deaths per year, mainly in children.

It would therefore be highly desirable to develop a vaccine.

Current vaccine candidates based on the RTS,S protein, which acts by blocking infection of *P. falciparum* in the liver, have achieved only partial efficacy. There is therefore a need for a vaccine which can emulate natural immunity by protecting against the disease-causing blood-stage *Plasmodium* parasite.

Previous studies have investigated the potential for antigens to induce antibodies which are effective against blood-stage malaria parasites in vitro, using the standard growth inhibitory activity (GIA) assay. One such antigen is apical membrane antigen 1 (PfAMA1).

GIA assay investigations into other protein families involved in blood-stage *Plasmodium* parasite invasion of RBCs have found them to be ineffective or less effective than PfAMA1.

PfAMA1 has therefore been a major focus of research on countering blood-stage malarial parasites. However, antibodies against PfAMA1 appear only to be effective at an extremely high concentration. In addition, PfAMA1 induces strain-specific antibodies which are not effective against genetically diverse strains of the *Plasmodium* parasite (A. L. Goodman, S. J. Draper, *Ann. Trop. Med. Parasitol.* 104, 189 (2010)). In addition, vaccine development has been hampered by the requirement for potentially reactogenic chemical adjuvants in addition to the antigen to induce sufficient antibody responses in human subjects.

There is a need for antigens which will induce antibodies that are effective even at lower concentrations of immunoglobulin. There is a need for antigens which will induce antibodies that are effective against genetically diverse strains of the *Plasmodium* parasite. There is a need for antigens that are effective without requiring potentially reactogenic chemical adjuvants.

The present invention addresses one or more of the above needs by providing antigens, vectors encoding the antigens, and antibodies (and antibody-like molecules including aptamers and peptides) that specifically bind to the antigen, together with the uses thereof (either alone or in combination) in the prevention or treatment of malaria.

In one aspect, the invention provides a Reticulocyte-binding protein Homologue 5 (PfRH5) antigen or a fragment thereof. In one embodiment, the PfRH5 antigen or fragment thereof is present in the form of a vaccine formulation.

The term antigen or fragment thereof, means any peptide-based sequence that can be recognised by the immune system and/or that stimulates a cell-mediated immune response and/or stimulates the generation of antibodies.

In another aspect the present invention provides a vector that expresses PfRH5 antigen or a fragment thereof. In one embodiment the vector is present in the form of a vaccine formulation.

The Reticulocyte binding Homologue (PfRH) family comprises six members (PfRH1, PfRH2a, PfRH2b, PfRH3, PfRH4 and PfRH5), each of which is involved in the binding of the *Plasmodium* parasite to RBCs, with the possible exception of PfRH3 which may be a non-expressed pseudogene. The PfRH family has been identified as adhesins on the surface of the merozoite form of the *Plasmodium* parasite, which bind to receptors on the surface of the erythrocyte and hence permit invasion of RBCs by the parasite in its blood-stage. The PfRH5 antigen has an approximate molecular weight of 63 KDa. In vitro cleaved fragments of approximately 45 KDa and 28 KDa have been reported.

The PfRH5 antigen of the present invention induces antibodies which are highly effective in the GIA assay against the blood-stage *Plasmodium* parasite. This is very surprising since earlier studies have failed to demonstrate that the PfRH5 antigen will induce anything other than antibodies which are ineffective or only poorly effective (i.e. substantially less effective than is commonly observed with PfAMA1-induced antibodies) in a GIA assay.

The antigen of the present invention surprisingly induces antibodies which neutralise parasites more effectively than PfAMA1 and remain effective at lower concentrations of immunoglobulin. In addition, the antigen induces antibodies which have also surprisingly been found to be effective against genetically diverse strains of the *Plasmodium* parasite, which is likely to be of critical importance in achieving vaccine efficacy against the variety of strains circulating in the natural environment.

This represents the first example of a highly effective cross-strain GIA against the *Plasmodium* parasite using a single antigen and therefore represents a major breakthrough in the treatment and prevention of malaria.

Thus, in one embodiment, the PfRH5 antigen or fragment thereof provides protection (such as long term protection) against disease caused by *Plasmodium* parasites.

In one embodiment, the PfRH5 antigen or fragment thereof provides an antibody response (e.g. a neutralising antibody response) to *Plasmodium* parasitic infection.

The present inventors have also found that even greater efficacy can be achieved through combining the PfHR5 antigen with one or more of other *P. falciparum* antigens. GIA assays involving such combinations have demonstrated an effect which is greater than the sum of inhibition with individual antibodies, i.e. a synergistic effect. This is surprising since the other members of the PfRH family do not appear to be particularly effective in the GIA assay.

Accordingly, in another aspect the present invention provides the Reticulocyte-binding protein Homologue 5 (PfRH5) antigen or a fragment thereof, and one or more antigens selected from the group consisting of PfAMA1, PfEBA175, PfRH2a, PfRH2b or PfRH4, or a fragment thereof. Particularly preferred embodiments include the PfRH5 antigen or a fragment thereof together with one or more of the PfEBA175, PfRH2a, PfRH2b or PfRH4 antigens or a fragment thereof. In one embodiment, the antigens or fragments thereof are present in the form of a vaccine formulation.

In a related aspect, the present invention provides a vector that expresses PfRH5 antigen or a fragment thereof, and one or more antigens selected from the group consisting of PfAMA1, PfEBA175, PfRH2a, PFrH2b or PfRH4, or a fragment thereof. In another aspect, the present invention provides a vector that expresses PfRH5 antigen or a fragment thereof, together with a further vector that expresses one or more antigens selected from the group consisting of PfAMA1, PfEBA175, PfRH2a, PFrH2b or PfRH4, or a fragment thereof.

Particularly preferred embodiments include a vector or vectors which express PfRH5 antigen or a fragment thereof together with one or more of the PfEBA175, PfRH2a, PfRH2b or PfRH4 antigens or a fragment thereof. In one embodiment, the vector or vectors are present in the form of a vaccine formulation.

In one embodiment of the invention, the vector is a viral vector. The viral vector may be an adenovirus (of a human serotype such as AdHu5, a simian serotype such as AdCh63, or another form) or poxvirus vector (such as a modified vaccinia Ankara (MVA)).

Viral vectors are usually non-replicating or replication impaired vectors, which means that the viral vector cannot replicate to any significant extent in normal cells (e.g. normal human cells), as measured by conventional means—e.g. via measuring DNA synthesis and/or viral titre. Non-replicating or replication impaired vectors may have become so naturally (i.e. they have been isolated as such from nature) or artificially (e.g. by breeding in vitro or by genetic manipulation). There will generally be at least one cell-type in which the replication-impaired viral vector can be grown—for example, modified vaccinia Ankara (MVA) can be grown in CEF cells.

Typically, the viral vector is incapable of causing a significant infection in an animal subject, typically in a mammalian subject such as a human or other primate.

In one embodiment, the vector is selected from a human or simian adenovirus or a poxvirus vector.

In a further embodiment of the invention, the vector is a DNA vector, such as a plasmid-based DNA vaccine. In one embodiment the DNA vector is capable of expression in a mammalian cell expression system.

In one embodiment, the PfRH5 antigen is defined by SEQ ID NO: 1. Alternatively, the antigen may be the mature form of the antigen in which the N-terminal signal peptide has been removed. By way of example, the mature form may comprise or consist of amino acid residues 26 to 526 of SEQ ID NO: 1. The present invention embraces fragments thereof, which comprise or consist of 170 consecutive amino acid residues or more in length (e.g. at least 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510 or 520 consecutive amino acid residues in length). The fragments of the invention have a common antigenic cross-reactivity with the PfRH5 antigen. In one embodiment the fragments of the invention do not comprise amino acids from the N-terminal signal peptide. In one embodiment the fragments of the invention comprise amino acid residues 191 to 359 of SEQ ID NO: 1. In one embodiment the fragments of the invention comprise amino acid residues 31 to 174 of SEQ ID NO: 1. In one embodiment the fragments of the invention comprise amino acid residues 304 to 430 of SEQ ID NO: 1.

The antigen or fragment thereof may have substitutions at amino acid residue 38 and/or at amino acid residue 214 of SEQ ID NO: 1, wherein the amino acid N is replaced by an amino acid other than N. In one embodiment the amino acid residue 38 and amino acid residue 214 are both replaced with Q.

The above-mentioned antigen or fragment thereof embraces variants exhibiting at least 90%, 91%, 92%, 93%, 94%, 95%, 96%, 97% 98% or 99% identity with SEQ ID NO: 1.

SEQ ID NO: 1 consists of 526 amino acid residues. Variants of SEQ ID NO: 1 are encompassed as set out above and may additionally or alternatively include amino acid sequences with one or more amino acid substitutions, deletions or insertions. Substitutions are particularly envisaged, as are N- and C-terminal deletions. Substitutions include conservative substitutions.

Thus, in one embodiment, a variant of SEQ ID NO: 1 comprises an N-terminal deletion of at least 1 consecutive amino acid residues (e.g. at least 30, 35, 40, 45 or 50 consecutive amino acid residues) in length.

Thus, in one embodiment, a variant of SEQ ID NO: 1 comprises a C-terminal deletion of at least 1 consecutive amino acid residues (e.g. at least 5, 10, 15, 20, 25, 30, 35, 40, 45 or 50 consecutive amino acid residues) in length.

In one embodiment, the vector expresses PfRH5 defined by SEQ ID NO: 2, including the secretory signal from bovine tissue plasminogen activator, or may include another signal to direct the subcellular trafficking of the antigen. Alternatively, the antigen may be the mature form of the antigen in which the N-terminal signal peptide has been removed. By way of example, the mature form may comprise or consist of amino acid residues 34 to 534 of SEQ ID NO: 2. The present invention embraces fragments thereof, which comprise or consist of 170 consecutive amino acid residues or more in length (e.g. at least 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510 or 520 consecutive amino acid residues in length). The fragments of the invention have a common antigenic cross-reactivity with the PfRH5 antigen. In one embodiment the fragments of the invention do not comprise amino acids from the N-terminal signal peptide.

The above-mentioned antigen or fragment thereof embraces variants exhibiting at least 90%, 91%, 92%, 93%, 94%, 95%, 96%, 97% 98% or 99% identity with SEQ ID NO: 2.

SEQ ID NO: 2 consists of 534 amino acid residues. Variants of SEQ ID NO: 2 are encompassed as set out above and may additionally or alternatively include amino acid sequences with one or more amino acid substitutions, deletions or insertions. Substitutions are particularly envisaged, as are N- and C-terminal deletions. Substitutions include conservative substitutions.

Thus, in one embodiment, a variant of SEQ ID NO: 2 comprises an N-terminal deletion of at least 1 consecutive amino acid residues (e.g. at least 35, 40, 45 or 50 consecutive amino acid residues) in length.

Thus, in one embodiment, a variant of SEQ ID NO: 2 comprises a C-terminal deletion of at least 1 consecutive amino acid residues (e.g. at least 5, 10, 15, 20, 25, 30, 35, 40, 45 or 50 consecutive amino acid residues) in length.

Conventional methods for determining amino acid sequence identity are discussed in more detail later in the specification.

As set out above, PfRH5 is a component of the mechanism by which the *Plasmodium* parasite invades RBCs. Compounds that specifically bind to PfRH5 inhibit this process and prevent the invasion of RBCs.

Accordingly, the present invention also provides binding compounds to Reticulocyte-binding protein Homologue 5 (PfRH5) antigen or a fragment thereof.

The present invention also provides binding compounds to PfRH5 antigen or a fragment thereof, in combination with binding compounds to any of PfAMA1, PfEBA175, PfRH2a, PfRH2b or PfRH4, or fragments thereof. Particularly preferred embodiments include binding compounds to the PfRH5 antigen or a fragment thereof in combination with binding compounds to one or more of the PfEBA175, PfRH2a, PfRH2b or PfRH4 antigens or a fragment thereof.

The binding compound may be an antibody, such as a monoclonal antibody or polyclonal antibody. The binding compound may be an antigen-binding fragment of a monoclonal or polyclonal antibody, or a peptide which binds to PrRH5 with specificity. The antibody may be a Fab, F(ab')2, Fv, scFv, Fd or dAb.

In another embodiment, the binding compound may be an oligonucleotide aptamer. The aptamer may bind to PfRH5 or a fragment thereof. The aptamer may specifically bind to PfRH5 or a fragment thereof.

Aptamers to PfRH5 have been found to inhibit *Plasmodium* parasite growth in a GIA assay. Such aptamers can be found by known methods (e.g. as set out in D. H. J. Bunka, P. G. Stockley, *Nature Reviews Microbiology* 4, 588 (2006)). The aptamer may be optimised to render it suitable for therapeutic use, e.g. it may be conjugated to a monoclonal antibody to modify its pharmacokinetics (e.g. half life and biodistribution) and/or recruit Fc-dependent immune functions.

The present invention also provides a method of stimulating or inducing an immune response in a subject comprising administering to the subject a PfRH5 antigen or fragment thereof, of the invention, or vector of the invention, or a binding compound of the invention (as described above).

Thus, in one embodiment, the method of stimulating or inducing an immune response in a subject comprises administering a PfRH5 antigen or fragment thereof, of the invention, or a vector of the invention, or a binding compound of the invention (as described above) to a subject.

In the context of the therapeutic uses and methods, a 'subject' is any animal subject that would benefit from stimulation or induction of an immune response against *Plasmodium* parasite. Typical animal subjects are mammals, such as primates, for example, humans.

In one embodiment, the present invention provides a method for treating or preventing malaria.

In one embodiment the present invention provides a PfRH5 antigen or fragment thereof, for use in prevention or treatment of malaria.

In a related aspect the present invention provides a PfRH5 antigen or fragment thereof, and one or more further antigens selected from the group consisting of PfEBA175, PfRH2a, PfRH2b or PfRH4, or a fragment thereof; for use in prevention or treatment of malaria.

In a further aspect the present invention provides the above vectors for use in prevention or treatment of malaria.

In yet a further aspect the present invention provides the above binding compounds for use in prevention or treatment of malaria.

In a further aspect, the present invention provides the use of the antigen or fragment thereof, vector, or binding compound of the invention (as described above) for use either alone or in combination in prevention or treatment of malaria.

In a related aspect, the present invention provides the use of the antigen or fragment thereof, vector, or binding compound of the invention (as described above), in the preparation of a medicament for the prevention or treatment of malaria.

In one embodiment, the method for treating or preventing malaria comprises administering a therapeutically effective amount of a PfRH5 antigen or fragment thereof, or binding compound, or a vector, of the invention (as described above) to a subject.

As used herein, the term "treatment" or "treating" embraces therapeutic or preventative/prophylactic measures, and includes post-infection therapy and amelioration of malaria.

As used herein, the term "preventing" includes preventing the initiation of malaria and/or reducing the severity or intensity of malaria.

A PfRH5 antigen or fragment thereof, or binding compound, or a vector, of the invention (as described above) may be administered to a subject (typically a mammalian subject such as a human or other primate) already having malaria, a condition or symptoms associated with malaria, to treat or prevent malaria. In one embodiment, the subject is suspected of having come in contact with *Plasmodium* parasite, or has had known contact with *Plasmodium* parasite, but is not yet showing symptoms of exposure.

When administered to a subject (e.g. a mammal such as a human or other primate) that already has malaria, or is showing symptoms associated with *Plasmodium* parasite infection, the PfRH5 antigen or fragment thereof, or binding compound, or a vector, of the invention (as described above) can cure, delay, reduce the severity of, or ameliorate one or more symptoms, and/or prolong the survival of a subject beyond that expected in the absence of such treatment.

Alternatively, a PfRH5 antigen or fragment thereof, or binding compound, or a vector, of the invention (as described above) may be administered to a subject (e.g. a mammal such as a human or other primate) who ultimately may be infected with *Plasmodium* parasite, in order to prevent, cure, delay, reduce the severity of, or ameliorate one or more symptoms of malaria, or in order to prolong the survival of a subject beyond that expected in the absence of such treatment.

The treatments and preventative therapies of the present invention are applicable to a variety of different subjects of different ages. In the context of humans, the therapies are applicable to children (e.g. infants, children under 5 years old, older children or teenagers) and adults. In the context of other animal subjects (e.g. mammals such as primates), the therapies are applicable to immature subjects and mature/adult subjects.

The PfRH5 antigen or fragment thereof, or a vector, of the invention (as described above) can be employed as vaccines.

In one aspect, the present invention provides a vaccine composition comprising the PfRH5 antigen of the invention or a fragment thereof.

In a related aspect, the present invention provides a vaccine composition comprising PfRH5 antigen or a fragment thereof, and one or more further antigens selected from the group consisting of PfAMA1, PfEBA175, PfRH2a, PfRH2b or PfRH4, or a fragment thereof. A particularly preferred embodiment provides a vaccine composition comprising PfRH5 antigen or a fragment thereof in combination with one or more of the PfEBA175, PfRH2a, PfRH2b or PfRH4 antigens or a fragment thereof.

In a further aspect, the present invention provides a vaccine composition comprising a vector that expresses PfRH5 antigen or a fragment thereof.

In yet a further aspect, the present invention provides a vaccine composition comprising a vector that expresses PfRH5 antigen or a fragment thereof, and one or more further antigens selected from the group consisting of PfAMA1, PfEBA175, PfRH2a, PfRH2b or PfRH4, or a fragment thereof. Alternatively, the present invention provides a vaccine composition comprising a vector that expresses PfRH5 antigen or a fragment thereof, together with a vector that expresses one or more further antigens selected from the group consisting of PfAMA1, PfEBA175, PfRH2a, PfRH2b or PfRH4, or a fragment thereof. A particularly preferred embodiment provides a vaccine composition comprising a vector or vectors that express PfRH5 antigen or a fragment thereof in combination with one or more of the PfEBA175, PfRH2a, PfRH2b or PfRH4 antigens or a fragment thereof.

As used, herein, a "vaccine" is a formulation that, when administered to an animal subject such as a mammal (e.g. a human or other primate) stimulates a protective immune response against *Plasmodium* parasitic infection. The immune response may be a humoral and/or cell-mediated immune response. A vaccine of the invention can be used, for example, to protect a subject from the effects of *P. falciparum* infection (i.e. malaria).

Preferably the vaccine of the invention comprises a PfRH5 antigen or fragment thereof which will result in a GIA of at least 30% and preferably at least 50% against the blood-stage *Plasmodium* parasite. Preferably the vaccine will confer such a result against a plurality of genetic strains of the blood-stage *Plasmodium* parasite.

The term "vaccine" is herein used interchangeably with the terms "therapeutic/prophylactic composition", "formulation" or "medicament".

The vaccine of the invention (as defined above) in addition to a pharmaceutically acceptable carrier can further be combined with one or more of a salt, excipient, diluent, adjuvant, immunoregulatory agent and/or antimicrobial compound.

Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of immunogenic compositions, therapeutic formulations, medicaments and prophylactic formulations (e.g. vaccines) is generally by conventional routes e.g. intravenous, subcutaneous, intraperitoneal, or mucosal routes. The administration may be by parenteral injection, for example, a subcutaneous or intramuscular injection. Formulations comprising neutralizing antibodies may be particularly suited to administration intravenously, intramuscularly, intradermally, or subcutaneously.

Accordingly, immunogenic compositions, therapeutic formulations, medicaments and prophylactic formulations (e.g. vaccines) of the invention are typically prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as BSA. In some embodiments, it may be desirable to formulate the composition with a preservative, such as thiomersal or sodium azide, to facilitate long term storage.

Examples of additional adjuvants which may be effective include but are not limited to: complete Freunds adjuvant (CFA), Incomplete Freunds adjuvant (IVA), Saponin, a purified extract fraction of Saponin such as Quil A, a derivative of Saponin such as QS-21, lipid particles based on Saponin such as ISCOM/ISCOMATIX, *E. coli* heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+ TDM+CWS) in a 2% squalene/Tween 80 emulsion.

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

The present invention encompasses polypeptides that are substantially homologous to polypeptides based on any one of the reference SEQ ID NOs identified in this application (including fragments thereof). The terms "sequence identity" and "sequence homology" are considered synonymous in this specification.

By way of example, a polypeptide of interest may comprise an amino acid sequence having at least 70, 75, 80, 82, 84, 86, 88, 90, 92, 94, 96, 98, 99 or 100% amino acid sequence identity with the amino acid sequence of a reference polypeptide.

There are many established algorithms available to align two amino acid sequences.

Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer implemented algorithms (eg. GAP, BESTFIT, FASTA or TFASTA), or BLAST and BLAST 2.0 algorithms.

The BLOSUM62 table shown below is an amino acid substitution matrix derived from about 2,000 local multiple alignments of protein sequence segments, representing highly conserved regions of more than 500 groups of related proteins (Henikoff & Henikoff, Proc. Natl. Acad. Sci. USA 89:10915-10919, 1992; incorporated herein by reference). Amino acids are indicated by the standard one-letter codes. The percent identity is calculated as:

$$\left[\frac{\text{Total number of identical matches}}{\begin{array}{c}\text{length of the longer sequence plus the number of gaps}\\\text{Introduced into the longer sequence in order}\\\text{to align the two sequences}\end{array}}\right] \times 100$$

BLOSUM62 table

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | 3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | 3 | -1 | 4 |

In a homology comparison, the identity may exist over a region of the sequences that is at least 10 amino acid residues in length (e.g. at least 15, 20, 30, 40, 50, 75, 100, 150, 200, 250, 300, 350, 400, 450, 500 or 520 amino acid residues in length)—e.g. up to the entire length of the reference sequence.

Substantially homologous polypeptides have one or more amino acid substitutions, deletions, or additions. In many embodiments, those changes are of a minor nature, for example, involving only conservative amino acid substitutions. Conservative substitutions are those made by replacing one amino acid with another amino acid within the following groups: Basic: arginine, lysine, histidine; Acidic: glutamic acid, aspartic acid; Polar: glutamine, asparagine; Hydrophobic: leucine, isoleucine, valine; Aromatic: phenylalanine, tryptophan, tyrosine; Small: glycine, alanine, serine, threonine, methionine. Substantially homologous polypeptides also encompass those comprising other substitutions that do not significantly affect the folding or activity of the polypeptide; small deletions, typically of 1 to about 30 amino acids (such as 1-10, or 1-5 amino acids); and small amino- or carboxyl-terminal extensions, such as an amino-terminal methionine residue, a small linker peptide of up to about 20-25 residues, or an affinity tag.

Key to SEQ ID NOs

SEQ ID NO: 1
Amino acid sequence of PfRH5 from 3D7 parasites,
NCBI XM_001351508.1.

SEQ ID NO: 2
Amino acid sequence of PfRH5FL vaccine antigen

SEQ ID NO: 1
MIRIKKKLILTIIYIHLFILNRLSFENAIKKTKNQENNLTLLPIKSTEEE

KDDIKNGKDIKKEIDNDKENIKTNNAKDHSTYIKSYLNTNVNDGLKYLFI

PSHNSFIKKYSVFNQINDGMLLNEKNDVKNNEDYKNVDYKNVNFLQYHFK

ELSNYNIANSIDILQEKEGHLDFVIIPHYTFLDYYKHLSYNSIYHKSSTY

GKCIAVDAFIKKINETYDKVKSKCNDIKNDLIATIKKLEHPYDINNKNDD

SYRYDISEEIDDKSEETDDETEEVEDSIQDTDSNHTPSNKKKNDLMNRTF

KKMMDEYNTKKKKLIKCIKNHENDFNKICMDMKNYGTNLFEQLSCYNNNF

CNTNGIRYHYDEYIHKLILSVKSKNLNKDLSDMTNILQQSELLLTNLNKK

MGSYIYIDTIKFIHKEMKHIFNRIEYHTKIINDKTKIIQDKIKLNIWRTF

QKDELLKRILDMSNEYSLFITSDHLRQMLYNTFYSKEKHLNNIFHHLIYV

LQMKFNDVPIKMEYFQTYKKNKPLTQ

SEQ ID NO: 2
MDAMKRGLCCVLLLCGAVFVSPSQEIHARFRRSENAIKKTKNQENQLTLL

PIKSTEEEKDDIKNGKDIKKEIDNDKENIKTNNAKDHSTYIKSYLNTNVN

DGLKYLFIPSHNSFIKKYSVFNQINDGMLLNEKNDVKNNEDYKNVDYKNV

NFLQYHFKELSNYNIANSIDILQEKEGHLDFVIIPHYTFLDYYKHLSYNS

IYHKSSTYGKCIAVDAFIKKIQETYDKVKSKCNDIKNDLIATIKKLEHPY

DINNKNDDSYRYDISEEIDDKSEETDDETEEVEDSIQDTDSNHTPSNKKK

NDLMNRTFKKMMDEYNTKKKKLIKCIKNHENDFNKICMDMKNYGTNLFEQ

LSCYNNNFCNTNGIRYHYDEYIHKLILSVKSKNLNKDLSDMTNILQQSEL

LLTNLNKKMGSYIYIDTIKFIHKEMKHIFNRIEYHTKIINDKTKIIQDKI

KLNIWRTFQKDELLKRILDMSNEYSLFITSDHLRQMLYNTFYSKEKHLNN

IFHHLIYVLQMKFNDVPIKMEYFQTYKKNKPLTQ

LIST OF FIGURES

FIG. 1: SDS-PAGE and Western blot analysis of cell lysates

Expression of the full-length PfRH5 antigen (RH5FL) from HEK293 mammalian cells transfected with a DNA plasmid (suitable for use as a DNA vaccine, or as a precursor for viral-vector vaccines or in vitro protein expression) was compared with expression of a PfRH5 fragment (RH5frag), by probing a Western blot using serum from mice immunised with viral vectors expressing RH5frag and mice immunised with other malaria antigens. Confirmation of expression of RH5FL was made by observation of a band at the 63 KDa region when probing with RH5frag-immunised sera. No such band was observed when the same sera was used upon a blot of lysate from cells transfected with a plasmid expressing another malaria antigen, nor when sera from mice immunised with non-RH5 malaria antigens were used to probe the RH5FL blot (data not shown).

Figure 2:
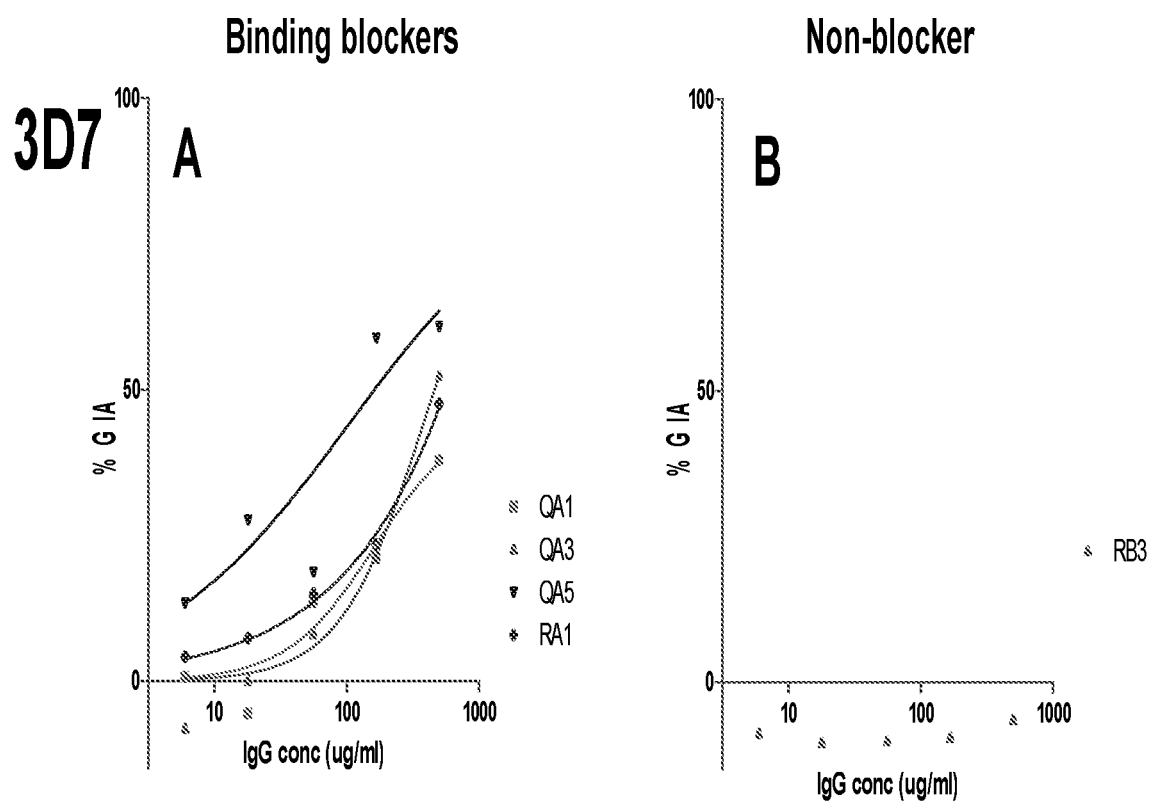

FIG. 2: Effects of anti-RH5 mAbs in GIA assay

Anti-RH5 mAbs were tested in GIA assays at a range of concentrations. Against 3D7 parasites, mAbs which had been shown by AVEXIS to block the interaction of RH5 and Basigin (BSG) all gave GIA (panel A) while the mAb which did not block the RH5-BSG interaction did not (panel B). A similar pattern was apparent against FVO parasites (at 500 ug/ml, QA1 resulted in 58% GIA; QA3 95%; QA5 91%; RA1 93%; and RB3 30%). Results displayed are the mean of two experiments with triplicate wells. Where shown, lines indicate four-parameter sigmoidal dose-response curves. The absence of a line for a particular mAb indicates failure of the nonlinear regression to converge, typically due to absence of a dose-response relationship.

Figure 3:
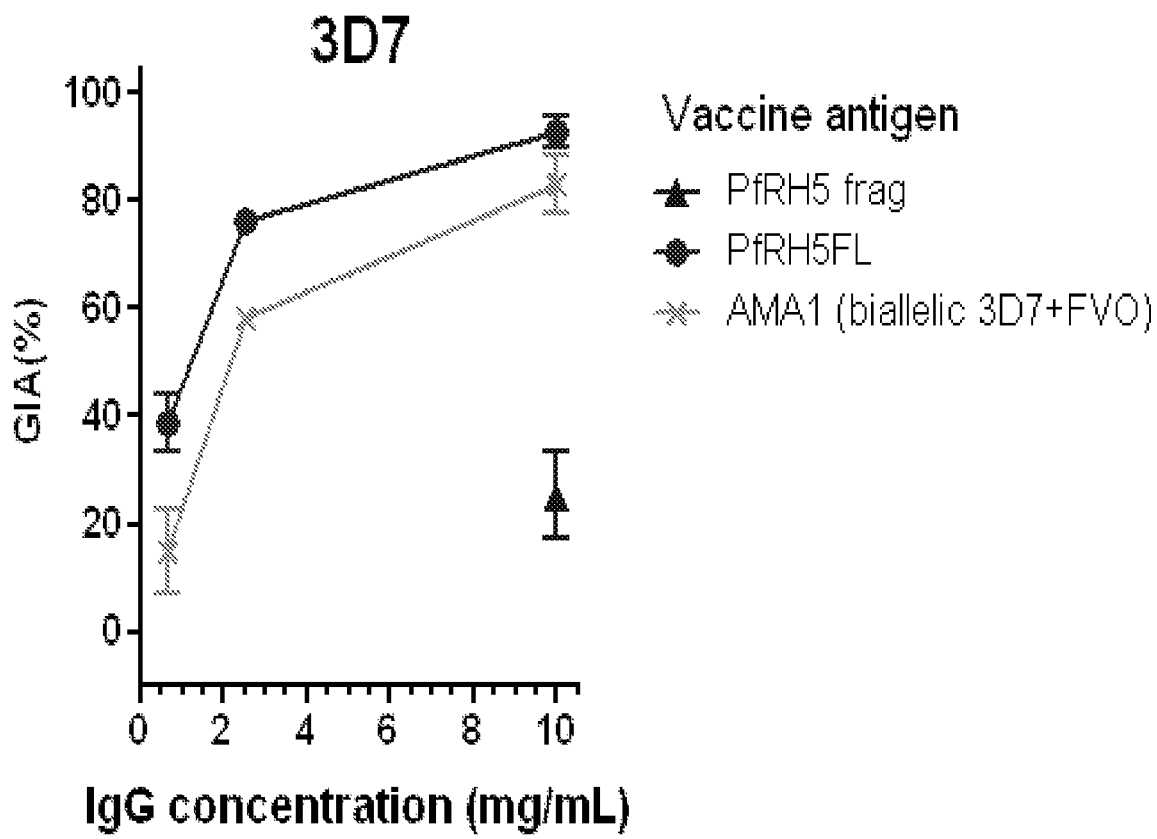

FIG. 3: Comparison of PfRH5 with PfAMA1 against 3D7 strain

The ability of vaccine-induced rabbit IgG to neutralize parasites in the widely-used assay of growth inhibitory activity (GIA) was investigated. IgG from all rabbits immunised with antigen was pooled. It was found that Anti-PfRH5FL (PfRH5FL) was substantially more effective than antibodies to the leading antigen PfAMA1 (AMA1) when tested against 3D7 parasites (the strain used for experimental human-challenge vaccine-efficacy trials, and upon which the vaccine antigen was based). It was also found that IgG induced by vectors expressing the antigen PfRH5FL (full-length reticulocyte-binding protein homologue 5) potently inhibited parasite growth, contrasting with modest inhibition by antibodies induced by vectors expressing an RH5 fragment (PfRH5 frag) which had previously been amenable to bacterial protein expression. Values are mean of two independent experiments, typically with three replicate wells. Error bars indicate inter-well SD.

FIG. 4: Comparison of PfRH5 with PfAMA1 against FVO strain (4A) and Dd2 strain (4B)

A GIA was carried out as above, using the same Anti-PfRH5FL (PfRH5FL) and two forms of PfAMA1: the first biallelic for 3D7 and FVO (3D7 and FVO); the second monoallelic for 3D7 (3D7). Two genetically distinct strains of parasite were used: the FVO (FIG. 4A) and Dd2 (FIG. 4B) strains. It was found that PfRH5FL-induced IgG was effective in GIA against both strains. By contrast, IgG induced by vaccination with 3D7-strain PfAMA1 was only weakly effective against either strain, while IgG induced by vaccination with a biallelic PfAMA1 vaccine (incorporating 3D7 and FVO-strain antigens) was only weakly effective against the Dd2 strain not included in the vaccine. Values are mean of two independent experiments with three replicate wells. Error bars indicate inter-well SD. Triangles: PfRH5FL; circles: PfAMA1 (3D7 and FVO); and crosses: PfAMA1 (3D7).

FIG. 5: Comparison of effects of PfRH5FL-induced IgG, IgG induced by vaccination with 3D7-strain PfAMA1, and IgG induced by vaccination with a bivalent PfAMA1 vaccine in assays of GIA against parasite strains 3D7 (5A), FVO (5B), Dd2 (5C), GB4 (5D), Camp (5E) and 7G8 (5F).

A GIA was carried out as above. Lines indicate dose-response curves fitted by non-linear least squares regression. All assays were performed using IgG purified from pooled serum of two PfRH5FL-vaccinated rabbits and single rabbits vaccinated with each PfAMA1 vaccine. Values are mean of two independent experiments with three replicate wells, with the exception of assays against 7G8 and Camp strains and monovalent PfAMA1 versus FVO (for which results are mean of three wells in a single experiment). Error bars indicate inter-well SD. Triangles: PfRH5FL (3D7); circles: PfAMA1 (3D7 and FVO); and crosses: PfAMA1 (3D7).

FIG. 6: Comparison of PfRH5 alone or with PfRH2a/b, PfRH4, PfEBA175 or PfAMA1

A GIA was carried out as above. Purified IgG from all rabbits immunised with the same antigen was pooled. The effect of IgG from pools with single antibody specificities was compared with the effects of mixing pools of two different specificities. It was found (FIG. 6A) that EBA175 alone had minimal effect, but that the effect of combining EBA175 with PfRH5 resulted in a synergistic increase in effectiveness. In a similar manner, it was found that RH2 (FIG. 6B) and RH4 (FIG. 6C) alone had no effect but that the effect of combining with PfRH5 resulted in a synergistic increase in both cases. In the case of combining PfRH5FL with anti-PfAMA1, a beneficial effect was also seen (FIG. 6D), which may have been additive rather than synergistic. Data points are mean of two independent experiments with three replicate wells.

EXAMPLES

The invention will be further clarified by the following examples, which are intended to be purely exemplary of the invention and are in no way limiting.

Unless otherwise stated, references to the full-length PfRH5 antigen (PfRH5FL) are to the antigen defined by amino acids 26 to 526 of SEQ ID NO: 1, ENAI . . . PLTQ, with substitutions N38Q and N214Q.

Example 1

Construction of PfRH Antigen, DNA Vectors, Viral Vectors, and PfRH5-Binding Agents PfRH5, a homologue of other PfRH proteins implicated in erythrocyte invasion, was originally identified from the *P. falciparum* genome sequence (K. Hayton et al., *Cell Host. Microbe* 4, 40 (2008)). Attempts to genetically knockout PfRH5 have failed, suggesting it is essential for parasite viability (J. Baum et al., *Int. J. Parasitol.* (2008)).

Sequencing of the PfRH5 gene in 18 laboratory parasite strains has revealed 10 sites of amino acid polymorphism. The 3D7 sequence was used throughout except where otherwise stated.

Construction of DNA Vector

A DNA plasmid encoding full-length PfRH5 (PfRH5FL), or a fragment thereof, and/or with the addition of an affinity-purification tag under the control of a mammalian promoter (such as the cytomegalovirus immediate-early promoter) was constructed.

The DNA plasmid is suitable for use as a DNA vaccine, or as a precursor for viral-vector vaccines or in vitro protein expression.

Construction of Antigens

Mammalian cells (such as adherent or suspension HEK293 cells) were transiently transfected with the above DNA plasmid (control cells were transfected with a plasmid encoding an irrelevant antigen).

Expression of the full-length antigen was demonstrated by SDS-PAGE and Western blot of cell lysates, probing the band with sera from mice immunized with viral vectors expressing a fragment of PfRH5 (FIG. 1). No such bands were observed on similar blots probed with naïve mouse serum, or serum from mice immunized with other malaria antigens.

A stable mammalian cell line expressing PfRH5FL was constructed.

PfRH5FL was purified from mammalian cell cultures infected with adenovirus and/or poxvirus vectors expressing PfRH5FL with an affinity purification tag.

PfRH5FL was expressed transiently or stably in yeast (e.g. *Pichia* or *Saccharomyces*), insect cells (e.g. S2, or baculovirus expression system), or cell-free expression systems (e.g. wheatgerm lysate).

*P. falciparum* antigens were codon-optimized for human expression (Geneart, Germany). Unless otherwise stated, antigens were based on the 3D7 strain. PfEBA175, PfRH1, PfRH2a/b, and PfRH4.9 constructs were based upon fragments known (e.g. from K. C. Pandey et al., *Mol. Biochem. Parasitol.* 123, 23 (2002); X. H. Gao et al., *Plos Pathogens* 4, (2008); T. Triglia et al., *Infect. Immun.* 69, 1084 (2001); and W. H. Tham et al., *Infection and Immunity* 77, 2427 (2009)) to include erythrocyte binding domains. The PfRH2a/b construct is based upon a sequence shared between the PfRH2a and PfRH2b genes. Remaining constructs encoded full-length proteins, omitting signal peptides and transmembrane domains where applicable. In some cases NetNGlyc-predicted N-glycosylation sites were removed by N-Q or S-A substitution.

Production of mono-allelic (3D7) and bi-allelic (3D7 and FVO) adenoviral- and MVA-vectored PfMSP1 and PfAMA1 antigens was carried out using known techniques (as set out in A. L. Goodman et al., *Infect. Immun.* (2010); and S. J. Draper et al., *J. Immunol.* (2010)). FVO has four amino acid differences from the 3D7 sequence.

GST-tagged PfRH2A9 was produced in a similar manner to PfMSP119 discussed above.

An N-terminally His6-tagged PfRH4 fragment (NCBI refseq XM_001351509 from 3D7 strain, amino acids 1329-1607, NHIK . . . NAYY, the most C-terminal region prior to the transmembrane domain, not overlapping with the vaccine antigen of the invention) was produced by cloning the fragment into the pTrcHisC plasmid (Invitrogen), transforming Rosetta-strain *E. coli*, inducing expression and purifying protein according to the instructions of the Qiagen Ni-NTA faststart kit (Qiagen, UK).

Construction of Viral Vectors

PfRH antigens, including full-length PfRH5 (PfRH5FL), were cloned into replication-deficient adenovirus human serotype 5 (AdHu5) and poxvirus (modified vaccinia virus Ankara, MVA) genomes downstream of a mammalian secretory signal (from bovine tissue plasminogen activator), and viruses prepared using known techniques (as set out in S. J. Draper et al., *Nat. Med.* 14, 819 (2008)).

Simian adenoviral vectors such as AdCh63 were prepared by cloning the PfRH5-based antigen into alternative viral genome backbones using standard methods. Immunogenicity of these vectors was demonstrated to be equivalent to the AdHu5-MVA regime in mice and/or rabbits.

Construction of PfRH5-Binding Monoclonal Antibodies

A murine monoclonal antibody which specifically bound PfRH5 protein in ELISA was isolated from hybridomas generated by fusing splenocytes from mice immunized with PfRH5FL with myeloma cells. It was confirmed that this antibody recognized native parasites in an indirect immunofluorescence assay, and inhibited parasite growth in GIA.

A panel of 5 mAbs was generated which were capable of binding RH5 by ELISA. Balb/c mice were immunised with adenovirus and MVA-vectored PfRH5FL vaccines, as previously described, at doses of $1 \times 10^8$ infectious units and $1 \times 10^7$ plaque forming units respectively, and with an 8 to 12 week prime-boost interval. Splenocytes were fused with Sp2 myeloma cells, according to previously published methods (Yokoyama, W. M et al. *Curr Protoc Immunol* (2006)). Hybridoma supernatants were screened for binding to recombinant PfRH5 protein by ELISA (a kind gift of Dr G Wright, Sanger Institute, Cambridge), using previously published methods.

The ability of each of the mAbs to neutralize 3D7-strain parasites was tested in a GIA assay. All 4 mAbs which were capable of blocking the RH5-BSG interaction in the AVEXIS assay were found to be capable of some degree of parasite neutralization, while the remaining mAb had no effect (FIGS. 2A & B).

Previously published methods were used to minimize the immunogenicity of the monoclonal antibody in order to make it suitable for human use, such as replacement of the murine Fc region with a human Fc region of a chosen Ig class and subtype.

Construction of PfRH5-Binding Polyclonal Antibodies

Polyclonal anti-PfRH5 was prepared by immunizing animals with PfRH5-based vaccines and purifying the resulting antibody e.g. on a PfRH5-protein affinity column.

Construction of PfRH5-Binding Aptamers

An oligonucleotide aptamer which specifically bound PfRH5 protein was identified using known methods (as set out e.g. in D. H. J. Bunka, P. G. Stockley, *Nature Reviews Microbiology* 4, 588 (2006)). It was confirmed that this molecule recognized native parasites in an indirect immunofluorescence assay, and inhibited parasite growth in GIA.

Previously published methods were used to optimize the pharmacokinetics (half life and biodistribution) of the aptamer, to render it suitable for therapeutic use.

The aptamer was conjugated to a monoclonal antibody to modify its pharmacokinetics and/or recruit Fc-dependent immune functions.

Example 2

Comparison In Vitro of PfRH Vaccine with Other Vaccine Candidate Antigens

Construction of Vectors

Vectors expressing the following antigens were generated:
PfEBA175, Genbank X52524 from Camp strain, amino acids 447-795, ELRE . . . RDDD, the 'F2' erythrocyte binding region (1).
PfMSP9, NCBI XM_001350647.1, amino acids 25-719, KNDK . . . EESK, with substitutions N529Q, N580Q, N621Q.
Pf38, NCBI XM_001351602.1, amino acids 23-327, VENK . . . REEI, with substitutions S166A, N294Q, S297A, N301Q.
PfRAP3, NCBI XM_001351538.1, amino acids 23-399, NKCK . . . NIFK, with substitutions N50Q, N246Q.
PfRH1, NCBI XM_002808591.1, amino acids 500-833, LQIV . . . LTN, with substitutions N685Q, N830Q.
PfRH2a, NCBI XM_001350047.1, amino acids 2030-2531, ELRE . . . MLLN, a sequence shared between PfRH2a and PfRH2b and termed PfRH2A9
PfRH4.9, NCBI XM_001351509, amino acids 28-766, PSKE . . . MQNI
PfRH5 fragment (PfRH5frag), NCBI XM_001351508.1, amino acids 191-359 of SEQ ID NO: 1, NSIY . . . IRYH PfRH5 full-length (PfRH5FL), NCBI XM_001351508.1, amino acids 26-526 of SEQ ID NO: 1, ENAI . . . PLTQ, with substitutions N38Q and N214Q.

Viruses which did not express malaria antigens (an AdHu5 virus without an antigen insert, and an MVA virus expressing an influenza antigen) were used where negative controls were required.

Preparation of Animals

New Zealand white rabbits (2-4 per group) were immunized with 0.7-4.5×10^8 infectious units of recombinant AdHu5 on day 0, 0.5-1×10^8 plaque forming units MVA on day 56, and, in the case of the PfRH2 and PfEBA175 groups, received a third immunization on day 114 with 100 μg of either PfRH2 or PfEBA175 recombinant protein mixed with 20 μL (18 μg) Abisco adjuvant (ISCOM Matrix M, Isconova, Sweden).

In the case of the full-length PfRH5 (PfRH5FL), the exact doses used were $2.5 \times 10^8$ infectious units of AdHu5, and $5 \times 10^7$ infectious units of MVA.

Serum was collected two weeks after final vaccination. The above-described negative control and a positive control (bi-allelic PfAMA1) were included in each study.

Assay of Growth Inhibitory Activity (GIA)

The assay of GIA was performed using the method of the MVI/NIH reference laboratory (as set out in K. Miura et al., *Clinical and Vaccine Immunology* 16, 963 (2009)). Total IgG was purified using Protein G (Pierce).

Results were calculated relative to growth in the presence of 10 mg/mL IgG from a rabbit immunized with non-malaria control vaccines.

It was found that IgG induced by vectors expressing the antigen PfRH5FL (full-length reticulocyte-binding protein homologue 5) potently inhibited parasite growth (FIG. 3), contrasting with modest inhibition by antibodies induced by vectors expressing an RH5 fragment which had been amenable to bacterial protein expression. Anti-PfRH5FL was substantially more effective than antibodies to the leading antigen PfAMA1 (FIG. 3) when tested against 3D7 parasites (the strain used for experimental trials, and upon which the antigen was based).

Sequencing of the PfRH5 gene in 18 laboratory parasite strains has previously revealed limited polymorphism (10 amino acid sites), Hayton, K. et al. *Cell Host Microbe* 4, 40-51 (2008). Five vaccine-heterologous parasite strains (FVO, Dd2, GB4, Camp and 7G8) were selected on the basis of their genetic divergence from 3D7's PfRH5 sequence, and their differing patterns of ligand-receptor invasion 'pathway' usage (Lobo, C. A. et al. *Mol. Biochem. Parasitol.* 149, 246-251, (2006)). Together, these strains included amino acid changes at every polymorphic locus previously identified (Hayton 2008).

FVO, Dd2, Camp and GB4 parasites are known to vary substantially from 3D7 parasites in their ability to invade *Aotus nancymaae* erythrocytes, a phenotype believed to be associated with PfRH5 polymorphisms which may affect receptor recognition (Hayton 2008). Of 18 laboratory strains for which the PfRH5 gene has been sequenced and *Aotus* RBC invasion efficiency quantified, FVO is most divergent from the 3D7 strain upon which the vaccine was based (Hayton 2008).

Figures 4A, 4B:
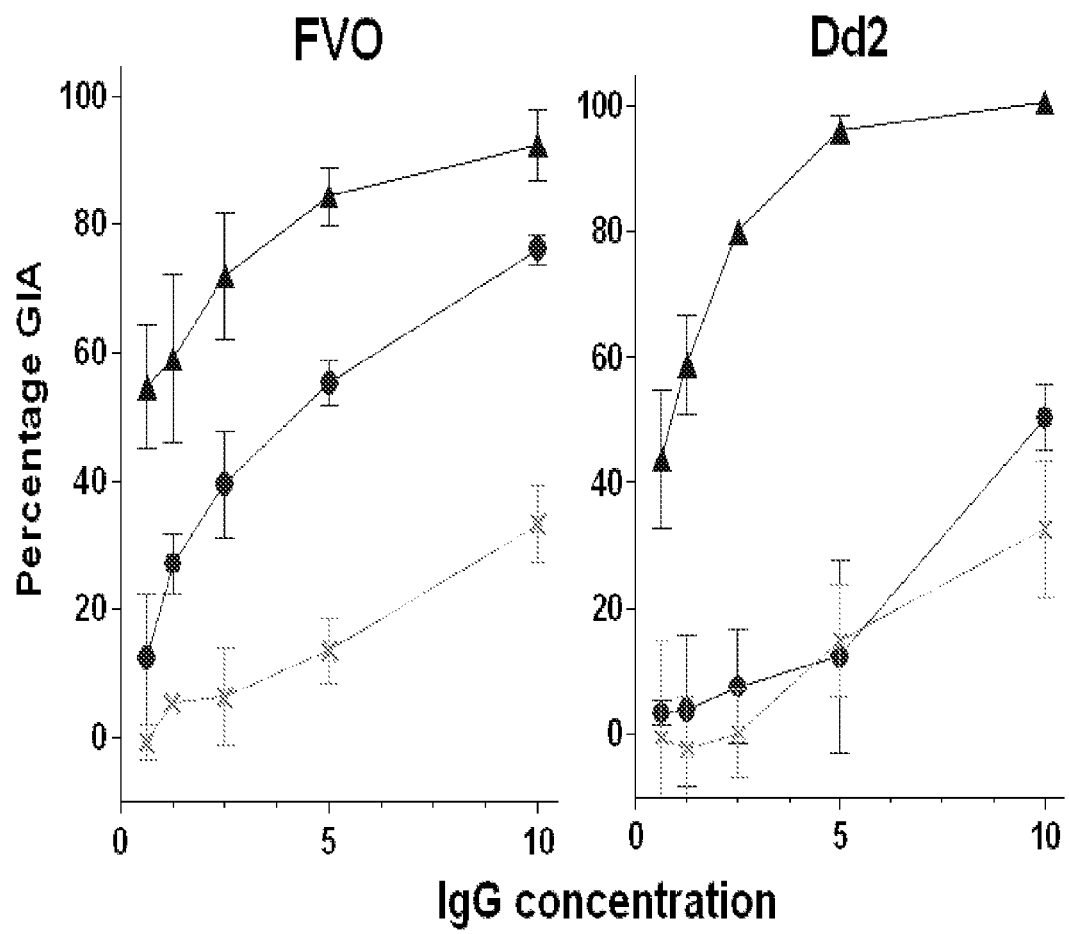

It was found that, despite the differences between the 3D7 sequence upon which the PfRH5FL was based and the FVO sequence, antibodies against this PfRH5FL remained equally effective against the genetically distinct parasite strains FVO and Dd2—a striking contrast to antibodies induced by both mono-allelic (3D7) and bi-allelic (3D7 and FVO) PfAMA1 antigen (FIGS. 4A and 4B).

Antibodies against PfRH5FL were found to be highly effective against all five additional parasite strains tested, in marked contrast to antibodies induced by both monovalent (3D7) and bivalent (3D7 and FVO) PfAMA1 vaccines (FIG. 5A to 5F).

$EC_{50}$ values were estimated for the GIA effect of anti-PfRH5FL and anti-PfAMA1 IgG against the various parasite strains. The $EC_{50}$ of anti-PfRH5FL was even lower against vaccine-heterologous parasite strains than against 3D7 parasites. Taken together with the higher $EC_{50}$ values for anti-PfAMA1 against vaccine-heterologous parasites, this resulted in a >5-fold reduction in $EC_{50}$ for anti-PfRH5FL relative to anti-PfAMA1 against all vaccine-heterologous parasite strains.

Assaying parasite growth inhibition by antigen-induced antibodies has thus identified the PfRH5 antigen as having greater effectiveness than the currently used PfAMA1 antigen and directly demonstrated strain-transcending antibody effects. The induction of this breadth of cross-strain parasite-neutralizing activity by a mono-allelic vaccine is surprising and demonstrates that PfRH5 provides an effective blood-stage malaria vaccine against *P. falciparum*.

Example 3

Comparison In Vitro of PfRH Antigen Alone with PfRH Antigen in Combination with Other Antigen Construction of Antigens This was carried out as for Example 2 above.

Preparation of Animals

This was carried out as for Example 2 above.

Assay of Growth Inhibitory Activity (GIA)

The assay of GIA was performed as for Example 2 above, with the exception that the RH4 vaccine used for this work was different from the one described above: it encoded amino acids 1329-1607 of PfRH4.

GIA was compared between wells containing IgG from PfRH5FL-immunized rabbits alone (at a range of concentrations) and wells containing anti-PfRH5FL plus 5 mg/ml of IgG purified from rabbits immunized with other antigens (immunization methods as described above).

The results are shown in FIG. 6. It was found that IgG for EBA175 (FIG. 6A), RH2 (FIG. 6B) and RH4 (FIG. 6C) gave 0-5% GIA when used alone. It was also found (not shown) that each IgG for EBA175, RH2 and RH4 gave <10% GIA when used alone at the higher concentration of 10 mg/ml. By contrast, the combination of EBA175, RH2 or RH4 with PfRH5FL gave a significantly greater GIA than PfRH5FL alone.

All results are relative to wells containing 10 mg/ml vector control-immunized rabbit IgG.

In a further experiment, the above protocol is repeated using PfRH5FL combined with IgG from rabbits immunised with other antigens, including Pf38, PfRAP3, PfMTRAP or full-length PfEBA175.

Synergistic neutralisation of parasites by antibodies with two or more distinct specificities could lower the total concentration of vaccine-induced antibody required to achieve protection against malaria, and hence facilitate the attainment of such protection by a multi-antigen vaccine. Such synergistic effects can be achieved by mixtures of anti-PfRH5 antibodies with anti-PfRH4 antibodies and by mixtures of anti-PfRH5 antibodies with anti-PfRH2 antibodies. These may thus be desirable antigen combinations for inclusion in a vaccine.

The Example has thus demonstrated that antibodies to a number of other *P. falciparum* antigens (including PfEBA175, PfRH2 and PfRH4) can act synergistically with antibodies to full-length PfRH5 in the assay of GIA, thus providing a multi-component vaccine. This effect appears to be a true synergy (greater than the sum of inhibition with antibodies of each individual specificity, and/or greater than the effect of doubling the concentration of antibody of either individual specificity).

Figure 6A:
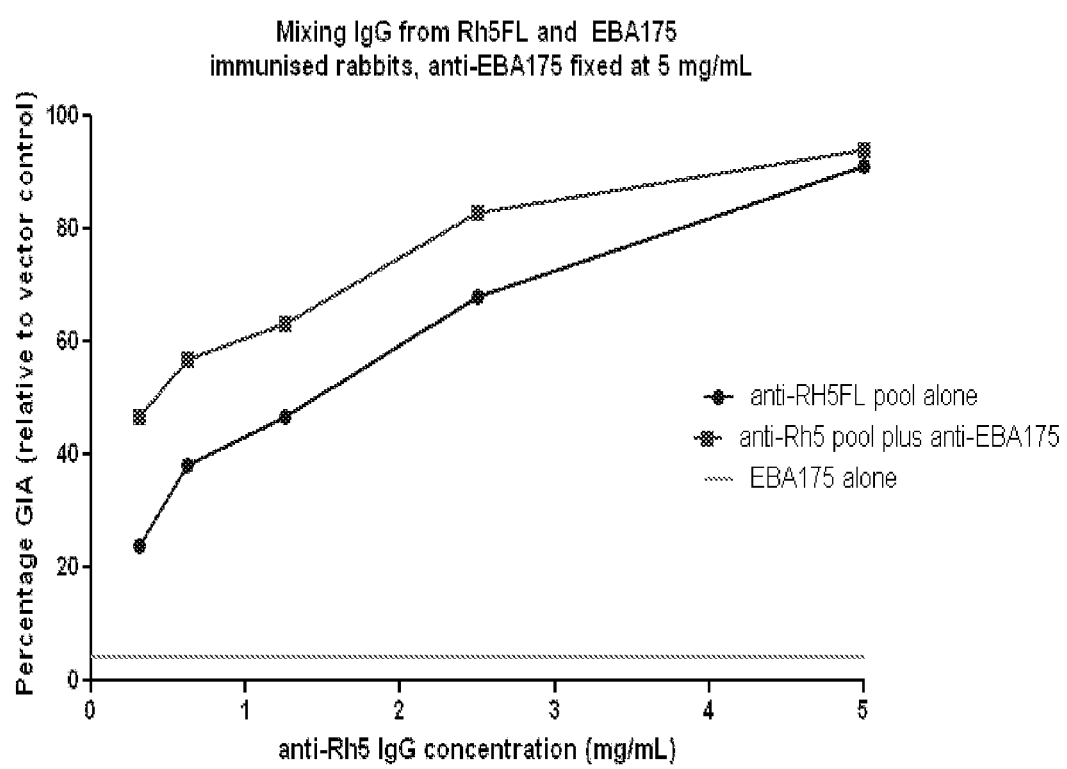
Figure 6B:
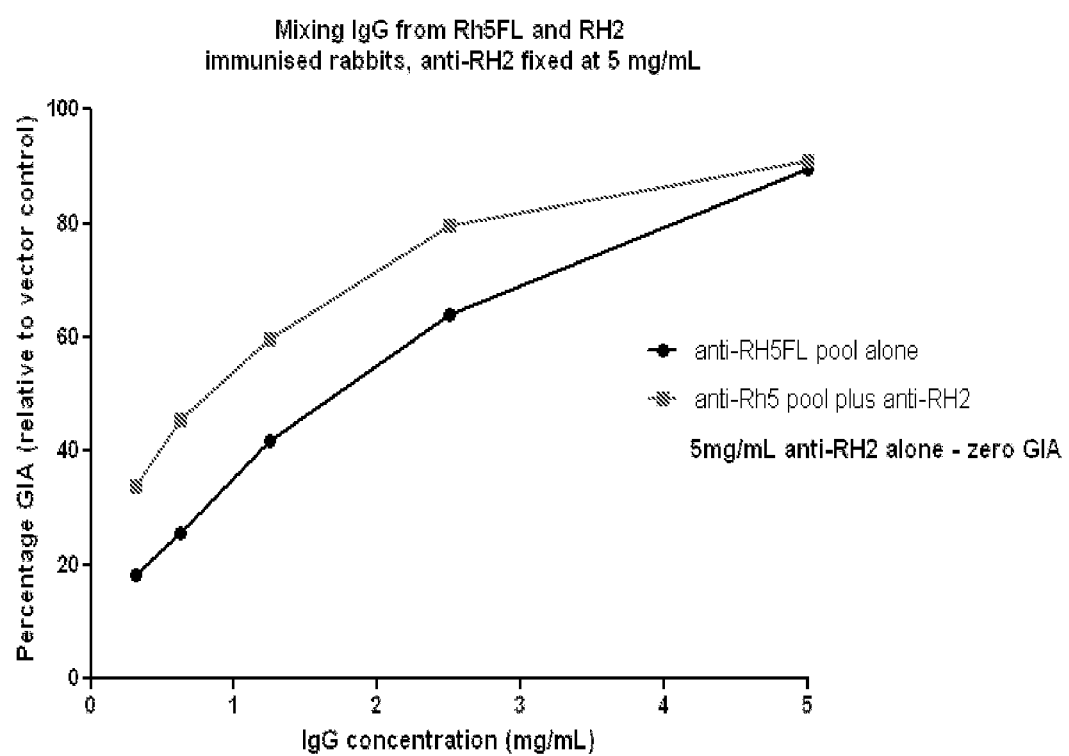
Figure 6C:
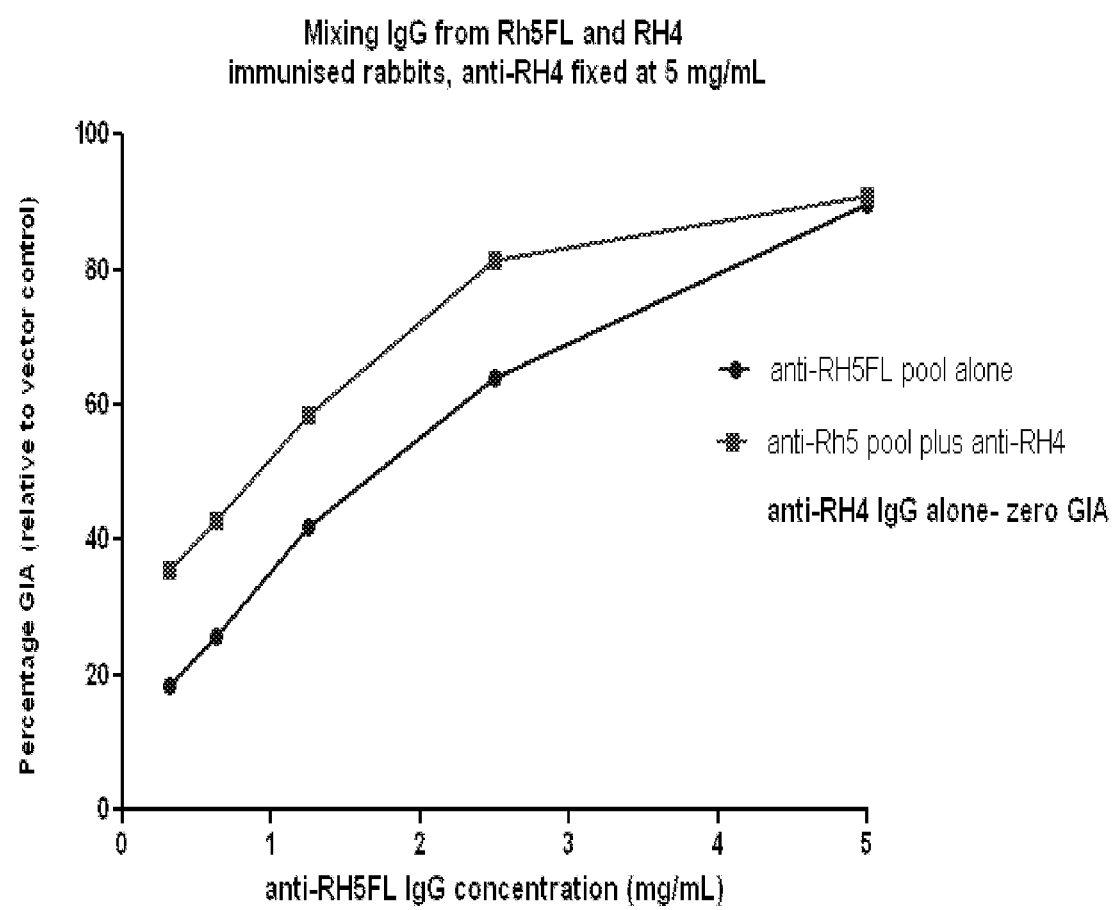
Figure 6D:
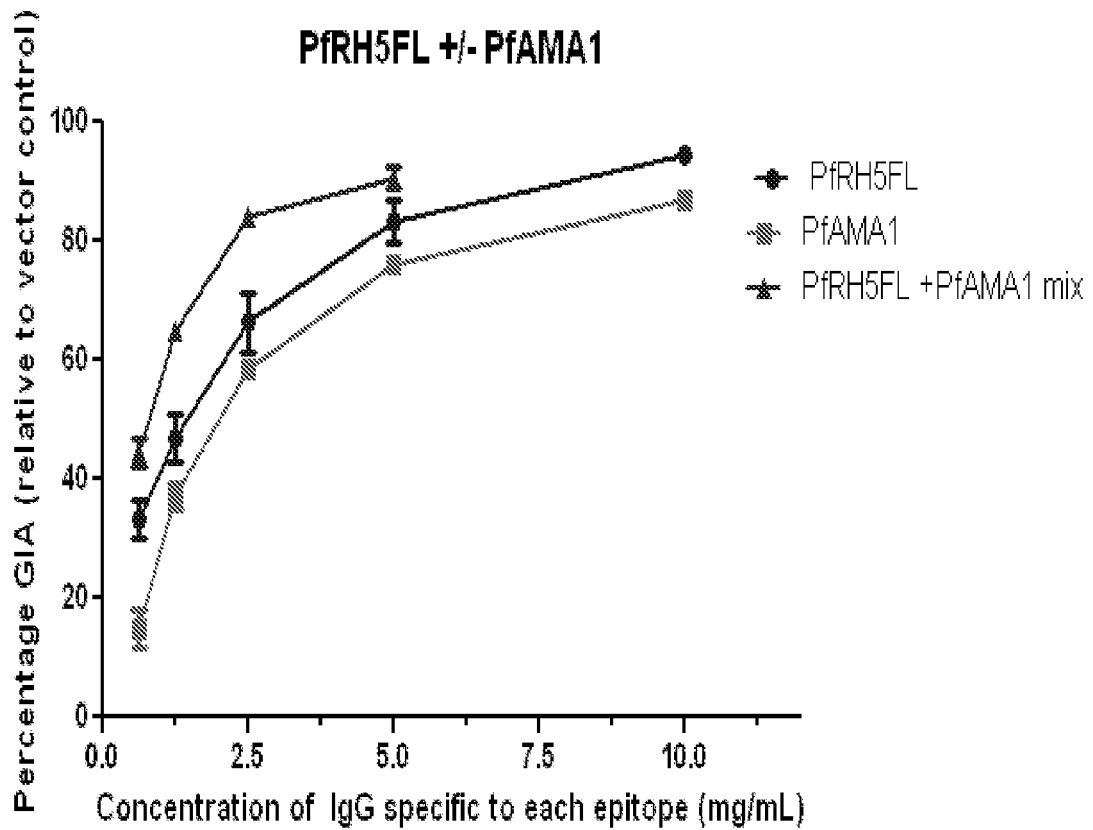

Additive, rather than truly synergistic, effects appear to be achieved when antibodies against PfRH5 and PfAMA1 are present together (FIG. 6D).

Example 4

In Vivo Use of PfRH Vaccine in Primates

Vaccine

The vaccines used are unadjuvanted replication-deficient viral vectors for full-length PfRH5 (PfRH5FL), with adenoviruses used for priming (likely serotype AdHu5 or AdCh63), and poxviruses used for boosting (Modified Vaccinia Ankara, MVA).

Viral vector vaccines are stored at −80 C or on dry ice prior to use, then thawed and are stable at 4 C/on ice for at least 2 hours. Vaccines are prepared for administration by dilution in PBS, which can be performed at an earlier date (followed by re-freezing) if necessary.

Doses to be used are calculated with reference to tolerability of vectored vaccines in humans, and doses used in previous rabbit studies with this antigen. The vaccines express blood-stage antigens of *P falciparum*. It has previously been demonstrated that these vaccines are immunogenic in mice and rabbits. The antibodies induced are highly effective in GIA, including against FVO parasites.

Preparation of Animals

*Aotus nancymaae* can be sourced from San Marcos University captive breeding programme and housed in AAALAC-accredited facilities at NAMRU-6.

Animals can be used which have previously been used in other studies, provided they are malaria-naive and have intact spleens. Possible confounding differences between animals (eg age, weight, type of previous use) could be addressed by stratified randomisation of animals to study groups.

Provisional group structure is as follows:

|  | Group number | Vaccine antigen | Number |
|---|---|---|---|
| VACCINE STUDY | 1 | AMA1 +/− MSP1 | 8 |
|  | 2 | PfRH5FL viral vectors | 8 |
|  | 3 | Empty vectors (no malaria antigen; negative control) | 8 |
| THERAPY STUDY | 4 | PfRH5 monoclonal antibody | 5 |
|  | 5 | PfRH5 aptamer | 5 |
|  | 6 | Untreated infection controls | 5 |
|  | N/A | N/A- challenge donor | 1 |
|  |  | Total | 40 |

Precise size and number of groups is determined with statistical advice, after review of the variability in outcomes in non-vaccinated control *Aotus* in previous *P. falciparum* challenge trials.

Administration of Vaccine

An 8 week prime-boost interval gives reliable immunogenicity in mouse, rabbit, macaque and humans with these and related vectors.

*P. falciparum* Challenge

Challenge is performed 2 weeks post-boost, at which time antibody responses were at or near maximum in a macaque study of related vectors (S. J. Draper et al., *J. Immunol.* (2010)).

Frozen vials of FVO parasites are available at NAMRU-6. Optimal dose of parasites to be used for challenge is determined by balancing improved reliability of outcome in negative control animals if higher dose used, versus possible improved sensitivity of efficacy detection with prolonged period of parasitaemia if a lower dose is used.

10,000 ring-stage parasites appear to be commonly used, obtained by dilution of blood of a donor monkey with microscopically-patent parasitaemia (S. Dutta et al., *Plos One* 4, (2009)).

The schedule is as follows:

Day −1:—Pre-immune bleed (c. 2 ml blood, for serum +/−PBMCs). This can be performed immediately prior to vaccination on day 0 if preferable for convenience of animal handling.

Day 0: Prime vaccination (adenovirus vectors in PBS, c. 200 ul intramuscular)

Day 14: Post-prime immuno-monitoring bleed (c. 2 ml blood, for serum +/−PBMCs)

Day 49: Optional immuno-monitoring bleed (0.5 ml blood, for serum)

Day 55: Pre-boost immuno-monitoring bleed (c. 2 ml blood, for serum +/−PBMCs). This can be performed immediately prior to boost vaccination on day 56 if preferable for convenience or animal handling.

Day 56: Boost vaccination (MVA vectors in PBS, 200-400 ul intramuscular)

Day 69=Day C-1: Post-boost immuno-monitoring bleed (c. 2 ml blood, for serum +/−PBMCs). This can be performed immediately prior to challenge on day 70 if preferable for convenience or animal handling.

Day 70=Day C+0: Challenge with FVO parasites. Dose and protocol TBC as above.

Daily from day C+3 until treatment endpoint: Clinical symptom scoring. Bleeds for parasitaemia monitoring by microscopy +/−QPCR; measurement of hematocrit and/or hemoglobin concentration. See below for treatment endpoints.

Day of treatment: Post-challenge immuno-monitoring bleed (0.5 ml blood, for serum)

~Day 91=Day C+21: End of challenge phase of study.

Re-challenge: a second challenge of the animals is envisaged.

Immunological and Parasitological Assays

Antigen-specific antibody titers are quantified by ELISA and/or LIPS at multiple timepoints.

Additional assays include:

GIA (pre-challenge timepoint; 70% GIA at 1:10 serum dilution has been proposed as a correlate of vaccine-induced protection in *Aotus*);

IFA (pre-challenge timepoint);

ADRB;

QPCR monitoring of parasite density

ELISPOT or ICS quantification of antigen-specific T cells.

Endpoints

Different possible endpoints have been proposed for *Aotus*-Pf challenges. Cumulative parasitemia calculated by summing daily parasitemia from the day of challenge until the day the first animal in the study is treated for any reason has been used in some recent studies and, by virtue of being a continuous variable, may have statistical advantages (J. A. Lyon et al., *Plos One* 3, (2008)).

Humane drug treatment endpoints are employed which may include the following:
- clinical symptoms exceeding a pre-defined score,
- a threshold level of uncontrolled parasitaemia eg 200,000 p/ul or 5%,
- a threshold level of anaemia,
- reaching a pre-specified day post-challenge, e.g. C+21.

Example 5

Use of PfRH Vaccine in Humans

Construction of Vaccine

Full-length viral-vector expressed PfRH5 (PfRH5FL) is generated from MVA, or AdHu5 or AdCh63. The process is initiated using a plaque-purified recombinant and GMP-certified HEK293 cells (available at the Jenner Institute Clinical Biomanufacturing Facility). A single batch of $>1.2 \times 10^{13}$ viral particles (vp) is generated. Release assays are according to the European Pharmacopoeia. Absence of replication competent virus is demonstrated. The MVA-PfRH5FL antigen is used as a boosting agent and is manufactured in chicken embryo fibroblasts (CEFs). The seed stock virus is supplied for production of the master seed virus/working seed virus (MSV/WSV). A clinical lot is then produced from the WSV. Vaccine toxicology studies are undertaken Administration of Vaccine Volunteers receive various dose schedules of viral-vector expressed PfRH5FL in groups. The sample size is sufficient to monitor routine and/or unexpected local and systemic AEs, whilst providing a thorough analysis of vaccine-induced cellular and humoral immunogenicity. Vaccine safety and immunogenicity is monitored in detail and analysed between dosing/regime groups using appropriate non-parametric statistics for small group sizes.

Vaccine-induced antigen-specific IgG function is assessed by in vitro assays of growth inhibitory activity (GIA) against *P. falciparum* strain 3D7, FVO and Dd2 parasites.

All vaccinations are administered intramuscularly in the deltoid muscle of the upper arm. This route of administration has been shown to be safe for other AdCh63 vaccines and to significantly reduce local AEs in comparison to intradermal vaccination.

Volunteers in Group 1 receive a dose of $5 \times 10^9$ vp of AdCh63 PfRH5FL (Group 1) and volunteers in Group 2 receive the full dose of $5 \times 10^{10}$ vp of AdCh63 PfRH5FL (Group 2). This two-step dose escalation for the AdCh63 vaccine vector has been applied to AdCh63-PfMSP1 and AdCh63-PfAMA1 in clinical trials without any safety issues arising.

Within Group 2 ($5 \times 10^{10}$ vp AdCh63-PfRH5FL), two sub-groups of volunteers (2B and 2C) are boosted after 8 weeks with an escalating dose of MVA-PfRH5FL. Group 2A represents non-boosted controls.

The doses of MVA-PfRH5FL are $1 \times 10^8$ pfu for Group 2B, and $2 \times 10^8$ pfu for Group 2C. A dose of $1-2 \times 10^8$ pfu is the standard dose currently used in other studies of MVA vaccines encoding ME-TRAP, PfMSP1 or PfAMA1.

Assessment Following Administration of Antigen

Safety and tolerability of viral-vector expressed PfRH5FL is assessed by comparing the frequency and severity of both local and systemic adverse events (AEs) between the dosing groups, including using diary cards for the first week. Details of AEs are collected at each clinic visit, along with a medical examination. Blood samples for haematology and biochemistry are taken at screening, and days 14, 28, 56, 63, 84 and 140.

Humoral and cellular immunogenicity of viral-vector expressed PfRH5FL vaccines administered in the various dosing regimes is assessed. Immunological blood samples are taken at screening and days 0, 1, 4, 7, 14, 28, 56, 57, 60, 63, 84, 112 and 140 with respect to AdCh63-PfRH5FL vaccination on day 0 and MVA-PfRH5FL vaccination on day 56.

PfRH5FL-specific immunogenicity is assessed by a variety of immunological assays including total IgG, isotype and avidity ELISA, memory B cell and plasma cell (ASC) ELIspot, ex-vivo IFN-γ ELISPOT, multiparameter flow cytometry and more exploratory assays including host gene expression studies post-vaccination.

Sporozoite Challenge

Once adequate immunogenicity is observed—defined as >20% GIA activity in at least half the vaccines—a further group of subjects vaccinated with the most immunogenic regime identified.

These subjects are challenged (along with non-vaccinated controls) with a number (e.g. 5) of infectious mosquito bites. This procedure is now well established by the Imperial College (R Sinden)—Oxford—Walter Reed (J Murphy) team and over 250 individuals have been challenged in the last six years.

Control volunteers develop patent parasitaemia at, on average, 11 days post challenge and those who do not develop malaria by day 21 are considered fully protected. The subjects are monitored carefully for any evidence of immunopathology (although this is very unlikely at the low parasite densities that are reached prior to treatment).

A real-time PCR assay to quantify blood-stage infection is used twice a day during the key follow-up period from day 6.5 to 14.0 post challenge (and daily thereafter). This has proved valuable in monitoring rates of parasite growth in vaccinees, recently providing evidence of measurable but low level blood-stage efficacy with the PEV3a vaccine.

Assessment Following Sporozoite Challenge

As in the above assessment following administration of antigen, detailed immunomonitoring is undertaken and, in this case, correlates of GIA activity and/or immune responses with efficacy are searched for.

Fully protected volunteers are invited to undergo a re-challenge at six months after their final vaccination to determine the durability of protection.

Example 6

In Vivo Treatment of Malaria in Primates Using PfRH-5 Binding Agents

Construction of Binding Agents

This is carried out as in Example 1 above.

Preparation of Animals

This is carried out as in Example 4 above.

*P. falciparum* Challenge

This is carried out as in Example 4 above, with the exception that malaria—and vaccine-naïve monkeys are infected with *P. falciparum* FVO parasites.

Treatment

At a pre-determined point at which all monkeys exhibit microscopically quantifiable parasitaemia, the therapeutic agents (monoclonal antibody or aptamer) are administered at high dose.

The dosage regime in the case of monoclonal antibody is in the region of 1 mg/ml blood volume. The dosage regime in the case of aptamers is the molar equivalent (around 7 μM)).

The outcome of infection is compared to infected but untreated control monkeys.

Immunological and Parasitological Assays

This is carried out as in Example 4 above.

Endpoints

These are considered as in Example 4 above.

---

The invention claimed is:

1. A vaccine composition comprising (i) an effective amount of an isolated, soluble Reticulocyte-binding protein Homologue 5 (PfRH5) antigen having at least 95% identity with amino acid residues 26 to 526 of SEQ ID NO: 1, said PfRH5 antigen lacking amino acid residues 1 to 25 of SEQ ID NO:1, and (ii) an effective amount of an adjuvant, wherein the vaccine provides protective immunity against *Plasmodium falciparum* infection.

2. The composition of claim 1, wherein the PfRH5 antigen has an amino acid other than N at residue 38 and/or at amino acid residue 214 of SEQ ID NO: 1.

3. The composition of claim 2, wherein the PfRH5 antigen has the amino acid Q at amino acid residue 38 and at amino acid residue 214 of SEQ ID NO: 1.

4. The composition of claim 1, wherein the composition further comprises one or more antigens from the group consisting of PfAMA1, PfEBA175, PfRH2a, PfRH2b or PfRH4, or a fragment thereof.

5. A method of treating or preventing malaria in a subject, comprising administering to the subject the vaccine composition of claim 1.

6. The method of claim 5, wherein the prevention or treatment comprises priming the subject with a human or simian adenovirus.

7. The method of claim 6, wherein the prevention or treatment further comprises boosting a subject with a pox virus.

8. The method of claim 5, wherein the PfRH5 antigen results in a GIA (growth inhibitory activity) of at least 50% against the blood-stage *Plasmodium falciparum* parasite.

9. The method of claim 8, wherein the PfRH5 antigen results in a GIA of at least 50% against a plurality of genetic strains of the blood-stage *Plasmodium falciparum* parasite.

10. The method of claim 5, wherein the vaccine confers pre-erythrocytic protection against *Plasmodium falciparum* parasites.

* * * * *

```
                        SEQUENCE LISTING

<160> NUMBER OF SEQ ID NOS: 2

<210> SEQ ID NO 1
<211> LENGTH: 526
<212> TYPE: PRT
<213> ORGANISM: Plasmodium falciparum

<400> SEQUENCE: 1

Met Ile Arg Ile Lys Lys Lys Leu Ile Leu Thr Ile Ile Tyr Ile His
1               5                   10                  15

Leu Phe Ile Leu Asn Arg Leu Ser Phe Glu Asn Ala Ile Lys Lys Thr
            20                  25                  30

Lys Asn Gln Glu Asn Asn Leu Thr Leu Leu Pro Ile Lys Ser Thr Glu
        35                  40                  45

Glu Glu Lys Asp Asp Ile Lys Asn Gly Lys Asp Ile Lys Lys Glu Ile
    50                  55                  60

Asp Asn Asp Lys Glu Asn Ile Lys Thr Asn Asn Ala Lys Asp His Ser
65                  70                  75                  80

Thr Tyr Ile Lys Ser Tyr Leu Asn Thr Asn Val Asn Asp Gly Leu Lys
                85                  90                  95

Tyr Leu Phe Ile Pro Ser His Asn Ser Phe Ile Lys Lys Tyr Ser Val
            100                 105                 110

Phe Asn Gln Ile Asn Asp Gly Met Leu Leu Asn Glu Lys Asn Asp Val
        115                 120                 125

Lys Asn Asn Glu Asp Tyr Lys Asn Val Asp Tyr Lys Asn Val Asn Phe
    130                 135                 140

Leu Gln Tyr His Phe Lys Glu Leu Ser Asn Tyr Asn Ile Ala Asn Ser
145                 150                 155                 160

Ile Asp Ile Leu Gln Glu Lys Glu Gly His Leu Asp Phe Val Ile Ile
                165                 170                 175

Pro His Tyr Thr Phe Leu Asp Tyr Tyr Lys His Leu Ser Tyr Asn Ser
            180                 185                 190

Ile Tyr His Lys Ser Ser Thr Tyr Gly Lys Cys Ile Ala Val Asp Ala
        195                 200                 205

Phe Ile Lys Lys Ile Asn Glu Thr Tyr Asp Lys Val Lys Ser Lys Cys
    210                 215                 220

Asn Asp Ile Lys Asn Asp Leu Ile Ala Thr Ile Lys Lys Leu Glu His
225                 230                 235                 240

Pro Tyr Asp Ile Asn Asn Lys Asn Asp Ser Tyr Arg Tyr Asp Ile
                245                 250                 255

Ser Glu Glu Ile Asp Asp Lys Ser Glu Glu Thr Asp Asp Glu Thr Glu
            260                 265                 270

Glu Val Glu Asp Ser Ile Gln Asp Thr Asp Ser Asn His Thr Pro Ser
        275                 280                 285

Asn Lys Lys Lys Asn Asp Leu Met Asn Arg Thr Phe Lys Lys Met Met
    290                 295                 300

Asp Glu Tyr Asn Thr Lys Lys Lys Leu Ile Lys Cys Ile Lys Asn
305                 310                 315                 320

His Glu Asn Asp Phe Asn Lys Ile Cys Met Asp Met Lys Asn Tyr Gly
                325                 330                 335
```

```
Thr Asn Leu Phe Glu Gln Leu Ser Cys Tyr Asn Asn Asn Phe Cys Asn
            340                 345                 350

Thr Asn Gly Ile Arg Tyr His Tyr Asp Glu Tyr Ile His Lys Leu Ile
            355                 360                 365

Leu Ser Val Lys Ser Lys Asn Leu Asn Lys Asp Leu Ser Asp Met Thr
        370                 375                 380

Asn Ile Leu Gln Gln Ser Glu Leu Leu Leu Thr Asn Leu Asn Lys Lys
385                 390                 395                 400

Met Gly Ser Tyr Ile Tyr Ile Asp Thr Ile Lys Phe Ile His Lys Glu
                405                 410                 415

Met Lys His Ile Phe Asn Arg Ile Glu Tyr His Thr Lys Ile Ile Asn
            420                 425                 430

Asp Lys Thr Lys Ile Ile Gln Asp Lys Ile Lys Leu Asn Ile Trp Arg
        435                 440                 445

Thr Phe Gln Lys Asp Glu Leu Leu Lys Arg Ile Leu Asp Met Ser Asn
        450                 455                 460

Glu Tyr Ser Leu Phe Ile Thr Ser Asp His Leu Arg Gln Met Leu Tyr
465                 470                 475                 480

Asn Thr Phe Tyr Ser Lys Glu Lys His Leu Asn Asn Ile Phe His His
                485                 490                 495

Leu Ile Tyr Val Leu Gln Met Lys Phe Asn Asp Val Pro Ile Lys Met
            500                 505                 510

Glu Tyr Phe Gln Thr Tyr Lys Lys Asn Lys Pro Leu Thr Gln
        515                 520                 525

<210> SEQ ID NO 2
<211> LENGTH: 534
<212> TYPE: PRT
<213> ORGANISM: Artificial
<220> FEATURE:
<223> OTHER INFORMATION: Vaccine antigen derived from Plasmodium
      falciparum PfRH5

<400> SEQUENCE: 2

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Ser Glu Asn Ala Ile Lys Lys Thr Lys Asn Gln Glu Asn Gln Leu Thr
        35                  40                  45

Leu Leu Pro Ile Lys Ser Thr Glu Glu Lys Asp Asp Ile Lys Asn
        50                  55                  60

Gly Lys Asp Ile Lys Lys Glu Ile Asp Asn Asp Lys Glu Asn Ile Lys
65                  70                  75                  80

Thr Asn Asn Ala Lys Asp His Ser Thr Tyr Ile Lys Ser Tyr Leu Asn
                85                  90                  95

Thr Asn Val Asn Asp Gly Leu Lys Tyr Leu Phe Ile Pro Ser His Asn
            100                 105                 110

Ser Phe Ile Lys Lys Tyr Ser Val Phe Asn Gln Ile Asn Asp Gly Met
            115                 120                 125

Leu Leu Asn Glu Lys Asn Asp Val Lys Asn Asn Glu Asp Tyr Lys Asn
        130                 135                 140

Val Asp Tyr Lys Asn Val Asn Phe Leu Gln Tyr His Phe Lys Glu Leu
145                 150                 155                 160

Ser Asn Tyr Asn Ile Ala Asn Ser Ile Asp Ile Leu Gln Glu Lys Glu
```

```
                    165                 170                 175
Gly His Leu Asp Phe Val Ile Ile Pro His Tyr Thr Phe Leu Asp Tyr
            180                 185                 190

Tyr Lys His Leu Ser Tyr Asn Ser Ile Tyr His Lys Ser Ser Thr Tyr
            195                 200                 205

Gly Lys Cys Ile Ala Val Asp Ala Phe Ile Lys Lys Ile Gln Glu Thr
            210                 215                 220

Tyr Asp Lys Val Lys Ser Lys Cys Asn Asp Ile Lys Asn Asp Leu Ile
225                 230                 235                 240

Ala Thr Ile Lys Lys Leu Glu His Pro Tyr Asp Ile Asn Asn Lys Asn
            245                 250                 255

Asp Asp Ser Tyr Arg Tyr Asp Ile Ser Glu Glu Ile Asp Asp Lys Ser
            260                 265                 270

Glu Glu Thr Asp Asp Glu Thr Glu Glu Val Glu Asp Ser Ile Gln Asp
            275                 280                 285

Thr Asp Ser Asn His Thr Pro Ser Asn Lys Lys Lys Asn Asp Leu Met
            290                 295                 300

Asn Arg Thr Phe Lys Lys Met Met Asp Glu Tyr Asn Thr Lys Lys Lys
305                 310                 315                 320

Lys Leu Ile Lys Cys Ile Lys Asn His Glu Asn Asp Phe Asn Lys Ile
            325                 330                 335

Cys Met Asp Met Lys Asn Tyr Gly Thr Asn Leu Phe Glu Gln Leu Ser
            340                 345                 350

Cys Tyr Asn Asn Asn Phe Cys Asn Thr Asn Gly Ile Arg Tyr His Tyr
            355                 360                 365

Asp Glu Tyr Ile His Lys Leu Ile Leu Ser Val Lys Ser Lys Asn Leu
            370                 375                 380

Asn Lys Asp Leu Ser Asp Met Thr Asn Ile Leu Gln Gln Ser Glu Leu
385                 390                 395                 400

Leu Leu Thr Asn Leu Asn Lys Lys Met Gly Ser Tyr Ile Tyr Ile Asp
            405                 410                 415

Thr Ile Lys Phe Ile His Lys Glu Met Lys His Ile Phe Asn Arg Ile
            420                 425                 430

Glu Tyr His Thr Lys Ile Ile Asn Asp Lys Thr Lys Ile Ile Gln Asp
            435                 440                 445

Lys Ile Lys Leu Asn Ile Trp Arg Thr Phe Gln Lys Asp Glu Leu Leu
            450                 455                 460

Lys Arg Ile Leu Asp Met Ser Asn Glu Tyr Ser Leu Phe Ile Thr Ser
465                 470                 475                 480

Asp His Leu Arg Gln Met Leu Tyr Asn Thr Phe Tyr Ser Lys Glu Lys
            485                 490                 495

His Leu Asn Asn Ile Phe His His Leu Ile Tyr Val Leu Gln Met Lys
            500                 505                 510

Phe Asn Asp Val Pro Ile Lys Met Glu Tyr Phe Gln Thr Tyr Lys Lys
            515                 520                 525

Asn Lys Pro Leu Thr Gln
            530
```